(12) United States Patent
Kunst

(10) Patent No.: US 8,177,775 B2
(45) Date of Patent: *May 15, 2012

(54) PORTABLE EQUIPMENT FOR ADMINISTRATION OF FLUIDS INTO TISSUES AND TUMORS BY CONVECTION ENHANCED DELIVERY TECHNIQUE

(75) Inventor: Mechthild Kunst, Regensburg (DE)

(73) Assignee: Antisense Pharma GmbH, Regensburg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/027,037

(22) Filed: Feb. 14, 2011

(65) Prior Publication Data

US 2011/0137289 A1    Jun. 9, 2011

Related U.S. Application Data

(63) Continuation of application No. 10/420,094, filed on Apr. 22, 2003, now Pat. No. 7,963,956.

(51) Int. Cl.
*A61M 31/00* (2006.01)
*A61M 37/00* (2006.01)
*A61K 9/22* (2006.01)

(52) U.S. Cl. .............. 604/890.1; 604/93.01; 604/288.01

(58) Field of Classification Search .................... 604/20, 604/65–67, 131–135, 153, 288.01–288.04, 604/890.1, 891.1, 93.01, 500, 504, 522; 128/DIG. 12, DIG. 13
See application file for complete search history.

(56) References Cited

U.S. PATENT DOCUMENTS 7,963,956 B2 *   6/2011   Kunst .................... 604/890.1

* cited by examiner

*Primary Examiner* — Matthew F DeSanto
(74) *Attorney, Agent, or Firm* — Mayer Brown LLP

(57) ABSTRACT

The present invention is directed to a device for a portable convection enhanced delivery system that allows administering liquids to specific locations within the body, especially tissues and tumors also allowing outsubject treatment. The application system comprises a portable extracorporal pump with a fluid reservoir that is connected via an infusion system to an infusion catheter placeable to any tissue or tumor the fluid should be administered to by high flow microperfusion. The system enables administration of fluids of any kind by convection enhanced delivery also in out-patient treatment. The system can be used for delivering various drugs, proteins, protein toxins, antibodies for treatment or imaging, proteins in enzyme replacement therapy, growth factors and viruses or oligonucleotides in gene therapy etc. The application methods as well as the surgical method to implant this device are enclosed to this invention.

27 Claims, 6 Drawing Sheets

Pump: Pegasus      Catheter: local, single-port    M. Bronskill
   Flow rate: 8 µl/min    Axis: Z                     M. McDonald
                                                       N. Konyer

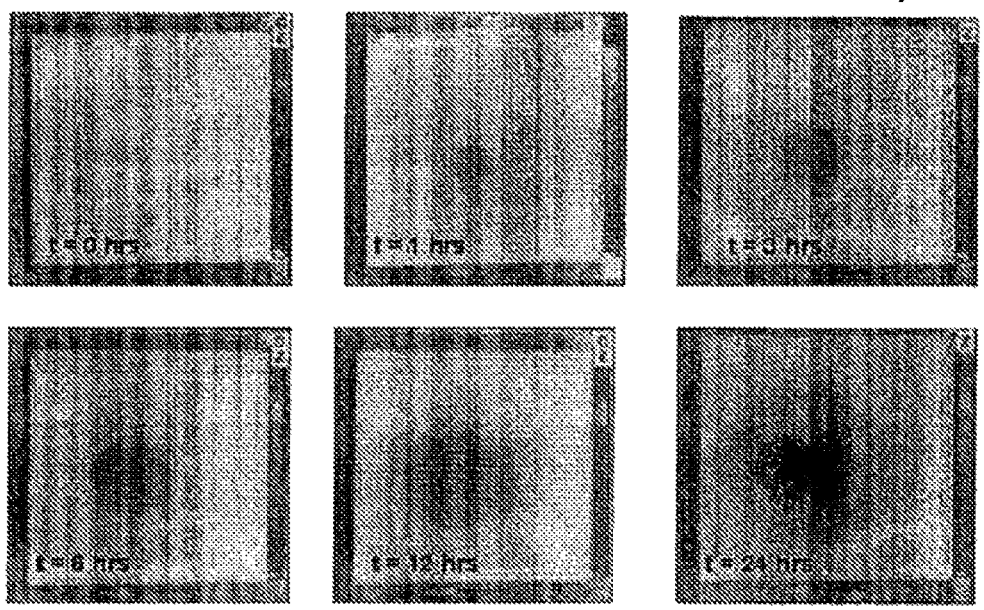

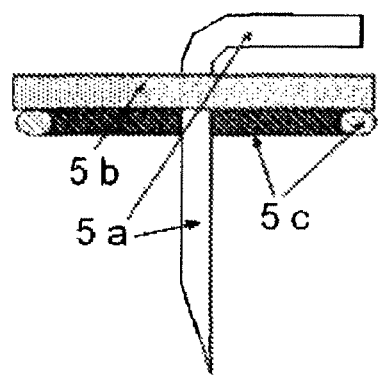
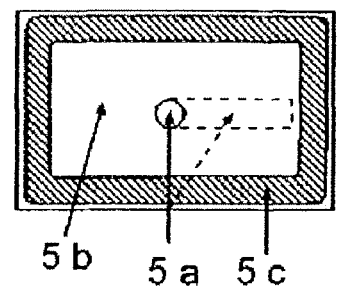
Figure 5 a:
Figure 5 b:
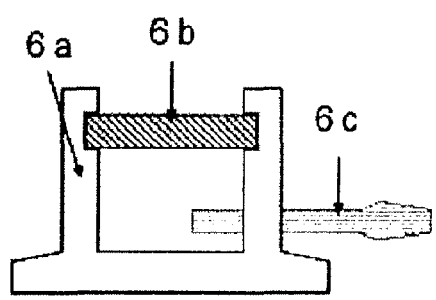
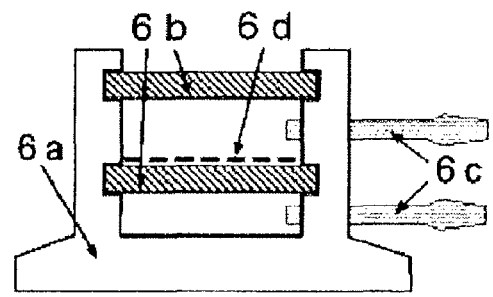
Figure 6:
Figure 8:
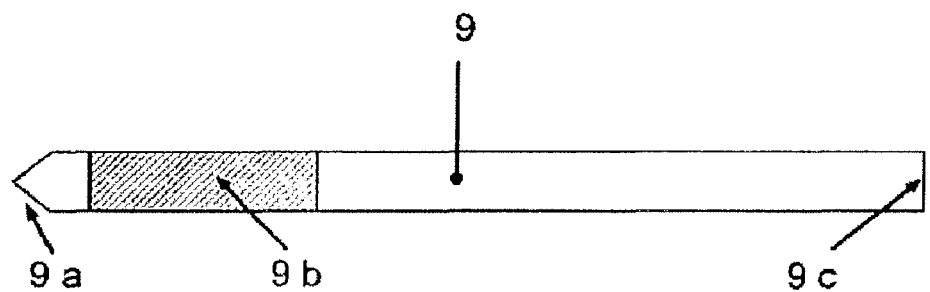
Figure 7:

PORTABLE EQUIPMENT FOR ADMINISTRATION OF FLUIDS INTO TISSUES AND TUMORS BY CONVECTION ENHANCED DELIVERY TECHNIQUE

CROSS-REFERENCE TO RELATED APPLICATIONS

This application is a continuation of U.S. patent application Ser. No. 10/420,094, filed Apr. 22, 2003.

FIELD OF THE INVENTION

The present invention relates generally to systems, kits, and methods of use for a medical device implantable in a subject's body. The system relates to a device for a convection enhanced delivery system, often regarded as high pressure microperfusion, comprising at least one pump with a fluid reservoir, an infusing system and an infusion catheter. The infusing system comprises at least a tube connecting the outlet of the pump with the infusion catheter. The methods for delivering drugs to a subject and implanting the device are also disclosed.

BACKGROUND OF THE INVENTION

A major hurdle in the development of many pharmaceutically active drugs is to find an appropriate delivery form for their administration in a subject to achieve a therapeutic level at the site of action. Additionally, if the target of the drug is a specific organ or a localized tumor, systemic administration may not be sufficient to reach effective drug concentrations at the target site to achieve the desired therapeutic effect. For example, many oligonucleotides or proteins, often of large molecular weights (for example, antibodies, hormones etc.), are found to be efficient drugs in vitro, but it is often problematic to reach an effective concentration of the drug at their in vivo target to illicit a therapeutic effect.

Another hurdle to overcome in administering drugs to a subject is crossing the blood-brain barrier. The blood brain barrier is very often an impenetrable obstacle for substances to cross even when the substances are administered intravenously. Difficulties in penetrating the blood-brain barrier can be traced to many causes, including, for example, a particular drug's chemical stability characteristics, its molecular weight, and/or its chemical charge and polarity etc.

Other drugs have toxic effects and therefore should only be administered locally. In the same context, imaging substances for example may best be suited for local administration to minimize systemic toxic side effects and/or improve their performance.

Existing techniques for regional drug delivery, such as impregnated polymer discs or bolus injections, depend on physical diffusion to distribute the agent. Often the distribution of large molecules is restricted and the rate of distribution is inversely related to the size of the agent and is slow relatively to tissue clearance. But even drugs with ideal characteristics for diffusion very often attain little satisfactory concentrations in the margins of the tissue or the tumor. In the case of lethal tumors, cell populations that exist beyond the site of drug delivery escape exposure to the drug because of inhomogeneous infusion determined to the concentration gradient that develops between the site of injection and the advancing tumor border.

For convection enhanced delivery of drugs into brain tissue a highly sophisticated delivery system has been described, see for example, PCT publication WO 95/05864. Substances are administered with a specific flow into a tissue or a tumor (for example, 0.5 to 15.0 µL/min) and the concentration of the drug spreads homogeneously around the infusion site. This convection enhanced delivery technique has only been possible with huge and heavy syringe pumps since the demand towards the continuity of flow characteristics is very high. The syringe pumps are described as being connected directly with the catheter which is positioned into the brain. Portable pumps used for the application of drugs into the vein, the interstitium or intraspinal applications have been regarded to have insufficient flow characteristics for this use. Also, a catheter directly accessing the target tissue can be used only during clinical treatment, but has to be renewed after some time (hours or days, for example) because the entrance has the potential to become infected.

The necessity for huge, non-portable syringe pumps and its direct combination with the catheter for implantation into the brain has restricted the use of this application system to in-patient treatment only. In particular, it is very inconvenient for the subject when the catheter is exposed or visible outside the body (for example, the head) during out-patient treatment. Beside this cosmetic disadvantage for the subject, the exposed catheter brings an additional risk of infection as the site of entry can be easily manipulated by mechanic strain. Furthermore, repeated surgery for implantation of a new catheter is desired in interval therapy. These surgeries are additional psychological obstacles as well, and involve a high risk of an additional infection and further complications for the subject.

The administration of drugs especially to the brain by indwelling pumps has also been describe in context with the treatment of movement disorders, see for example, U.S. Pat. No. 5,711,316, or with neurodegenerative disorders, see for example, U.S. Pat. No. 5,735,814. Whereas the technique of these apparatus is highly sophisticated, comprising a sensor as well, it would not fit the demands of convection enhanced delivery administration into a brain tumor. For example, these pumps have insufficient flow characteristics to be used in this application. Additionally, in the administration of fluids over a long period of time (for example, days, weeks or months) the electric supply of the pump will likely require recharging or replacement leading to further surgical intervention. Furthermore, for interval treatment in combination with huge volumes of solvents the supply of these solvents has to be extra-corporal or else otherwise additional surgeries would be necessary.

The administration of substances periodically via a access port system that can be connected with a catheter has also been described, see for example, U.S. Pat. No. 5,897,528. Access ports are in general chambers covered with a septum, which enables repeated puncture with a needle. The access port is connected via a access port catheter and a connector with an infusion catheter. This system allows repeated administration of pharmaceutical fluids. The positioning of the catheter during periodic administration of drugs as so far described, is restricted to body fluids (for example, interstitial fluids) because by implanting the catheter into a tumor or tissue, the openings of the catheter become overgrown with cells, especially tumor cells, when located herein and closed thereby during the time no solvent is administered.

Therefore, there remains a need for the administration of a therapeutic agent to a subject with continuous flow by employing convection enhanced delivery technique during out-patient treatment that is suitable for interval therapy, minimizes the number of surgeries needed for implantation and maintenance, is convenient to handle and/or is comfortable to wear during use. A faster onset of action, improved side-effect profile, enhanced stability, reduced dosing amount and frequency, and improved patient compliance are also desired for the delivery of therapeutic agents to a subject. In addition, it would be much desired to have a system having an indwelling pump and a catheter that can be located intrathecally. The discussion that follows discloses delivery systems, kits, and methods that help to fulfill these needs.

SUMMARY OF THE INVENTION

The effective administration of a fluid pharmaceutical agent to a specific location within a subject is complicated by the complexities of an in vivo system and the agent's physical and chemical properties. A device has been discovered that effectively delivers a therapeutically-effective amount of a liquid pharmaceutical agent to a subject that allows administration of the agent to a specific location within a subject, for example, a particular tissue or tumor. In one embodiment of the present invention, a portable convection enhanced delivery system administers a pharmaceutical agent in a liquid form to a specific location within a subject. In yet another embodiment of the present invention, the system comprises a portable extracorporal pump with a fluid reservoir that is connected via an infusion system to an infusion catheter implantable in a tissue or tumor of a subject. The fluid in one embodiment of the present invention, is administered by high flow microperfusion. The system can be used for delivering various therapeutic agents, such as, for example, drugs, proteins, protein toxins, imaging agents, antibodies for treatment or imaging, proteins in enzyme replacement therapy, growth factors, and/or viruses or oligonucleotides in gene therapy, etc. These delivery systems have been found to improve bioavailability and safety, as well as improve the pharmacokinetic and pharmacodynamic properties of the delivered therapeutic agent. The present invention also enables for the first time out-patient treatment with convection enhanced delivery technique using a portable pump. The present invention comprises these delivery systems, kits based thereon, and methods for the preparation and use thereof.

BRIEF DESCRIPTION OF THE DRAWINGS

Other advantages of the present invention will be readily appreciated as the same becomes better understood by reference to the following detailed description when considered in connection with the accompanying drawing wherein:

FIG. 2a depicts the flow characteristic at a set flow of 240 µL/h

FIG. 3a depicts the flow characteristic at a set flow of 240 µL/h. FIG. 3b shows the flow characteristic at a set flow of 480 µL/h.

FIGS. 4a and 4b depict the distribution of Evans blue dye in an isotropic 0.4% agarose gel which is proved to be an appropriate model to simulate brain diffusion characteristic. Images were taken at 0, 1, 3, 6, 12 and 24 hours of infusion time. FIG. 4a depicts the distribution of the radial piston pump "Pegasus Vario" at a flow of 480 µL/h, whereas FIG. 4b depicts the distribution of the high sophisticated syringe pump "Graseby® 3200" so far used for convection enhanced delivery technique at a flow of 480 µL/h.

FIGS. 5a and 5b depict an access system, comprising an access port needle (5a) bent with an angle of 90°, and a transparent cap (5b), that is lined by a ring of soft material (5c). FIG. 5a depicts the sectional view, FIG. 5b depicts the view from below.

FIG. 6 depicts the sectional view of an access port with one chamber with the casing (6a), a septum at the distal end (6b) and an outlet at the proximal end (6c).

FIG. 7 depicts schematic side view of an infusion catheter (9) with its tip at the proximal end (9a), the entrance at the distal end (9c) side and a region (9b) where the perfusion holes are arranged.

FIG. 8 depicts a sectional view of an access port with two port chambers with the casing (6a), two septa at the distal end of each chamber (6b) and two outlets (6c), one for each chamber, and a needle screen covering one of the chambers (6 d).

DETAILED DESCRIPTION OF THE INVENTION

Figure 1:
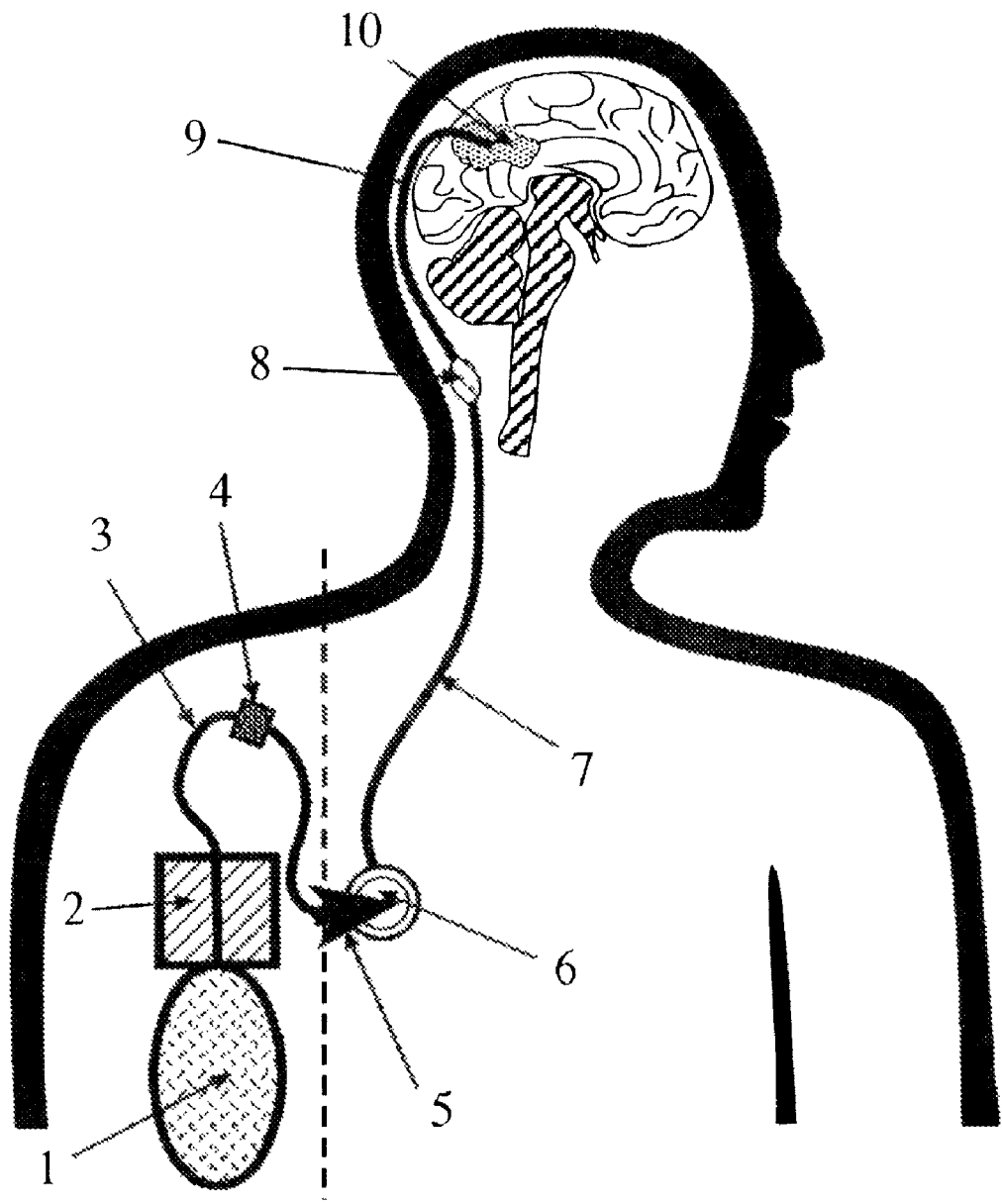
FIG. 1 shows an apparatus comprising a portable pump (2) with a solvent reservoir (1), an infusion tube (3) with a filter (4), an access system (5) (access port needle), connecting the infusion tube with an access port (6), an access port catheter (7) connected with a connector (8) with one infusion catheter (9), which is positioned with its perfusion holes into the target (10), tissue or tumor. The device left hand of the broken line is extracorporal, and right hand of the broken line are indwelling.

Referring to the drawings, the application system according to this invention enables the administration of substances dispersed or dissolved in, for example, an aqueous media, even in large volumes, during several hours, days, weeks, months, or years of treatment to a tissue or tumor by convection enhanced delivery technique.

Initially referring to FIG. 1, one embodiment of an apparatus of the present invention is shown. This particular embodiment comprises a portable pump (2) with a solvent reservoir (1), an infusion tube (3) with a filter (4), an access system (5) (access port needle), connecting the infusion tube with an access port (6), an access port catheter (7) connected with a connector (8) with one infusion catheter (9), which is positioned with its perfusion holes into the target (10), tissue or tumor. The portions of the device on the left hand of the broken line are extracorporal, and on the right hand side of the broken line are indwelling.

Referring to FIGS. 5a and 5b, one embodiment of an access system is shown that comprises an access port needle (5a) bent at an angle of 90°, and a transparent cap (5b), that is lined by a ring of soft material (5c). The scope of the top as well as the angle may differ from that shown. FIG. 5a depicts the sectional view, FIG. 5b depicts the view from below.

Referring to FIG. 6, a sectional view of one embodiment of an access port is shown comprising one chamber with the casing (6a), a septum at the distal end (6b), and an outlet at the proximal end (6c).

Referring to FIG. 7, a schematic side view of one embodiment of an infusion catheter (9) is shown with its tip at the proximal end (9a), the entrance at the distal end (9c) side and a region (9b) where the perfusion holes are arranged.

Referring to FIG. 8, a sectional view of one embodiment of an access port is shown containing two port chambers with the casing (6a), two septa at the distal end of each chamber (6b), and two outlets (6c), one for each chamber, and a needle screen covering one of the chambers (6 d).

The portability of the pump-system allows infiltrating the target (for example, a tissue or a tumor) with a soluble or suspended drug without limitation to in-subject treatment.

In one embodiment, the application system is configured for out-patient application.

The portable application system further enables rinsing the implanted catheter with a physiological fluid to prohibit its clogging by cellular growth during the time when no drugs are administered. Thus, interval therapies, without repeated surgery for implanting a new infusion catheter, becomes possible.

In addition, the pump in combination with a access port system opens an easy procedure to remove the pump for supplementary procedures such as maintaining or exchanging the pump and/or the infiltration tube, recharging the batteries, refilling the reservoir and/or changing the infiltration fluid, which can be useful for long term and interval administration and which has not typically been possible without additional surgery by an implanted pump.

The convection enhanced delivery application systems according to the state of art comprise only an infusion catheter and a heavy non-portable syringe pump. In one embodiment of the present invention, the apparatus utilizes a light weight portable pump and an additional access port system. In yet another embodiment of the present invention, the infusion catheter, the connector and the access port system are completely indwelling. In another embodiment of the present invention, the infusion catheter, the connector and the access port system with the access port catheter are completely indwelling. The entrance into the body is reduced to a small needle that is covered by a transparent cap with a soft lining in one embodiment. This device reduces the danger of contamination and infections coming from the puncture site. In case of changing components of the apparatus, for example, the fluid reservoir, the access port needle can be exchanged by a sterile one.

Using an access port system in combination with an infusion catheter for the administration of a substance dispersed or dissolved in fluids into tumors or tissues opens the widespread advantages of access port systems also for the field of, for example, convection enhanced delivery application where access port systems have not used to date. In one embodiment of the present invention, the infusion catheter is in fluid communication with an access port catheter and an access port is surgically implanted such that both of these can be completely indwelling. Thus the entrance into the body is reduced to the access port site. In one embodiment the access to the access port is a small access port needle covered by a transparent cap with a soft lining.

Furthermore the access port system can be positioned at any appropriate location favourable to the position of the portable pump, and/or to the convenience of the subject, and/or to the mechanic stability of the access port system (for example, over a rip).

The use of an access port system in combination with an infiltration catheter allows for exact placement of the infusion catheter in a one step surgical procedure into the center of a tissue or tumor. In another step, the access port system can be positioned in appropriate manner (for example, over a rip) and the access port catheter then can be laid slackly toward the entrance of the infusion catheter. In another step the two implanted catheters can be substantially permanently connected with an appropriate connector. This not only allows additional surgical procedures, but can also take into account the influence of mechanic stress at the position of the infusion catheter. The position of the infusion catheter can be located to minimize such mechanical stress.

The present invention of using a access port system in combination with an infusion catheter for the administration of substances dispersed or dissolved in fluids into rapidly growing tumors or tissues opens the widespread advantages of access port systems for the field of, for example, convection enhanced delivery application, which has not previously been described in the art.

In contrast thereto, diffusion using a pressure gradient-dependent convection-enhanced delivery of therapeutic agents has shown to produce a bulk flow current that has the potential to homogeneously distribute even large molecules through much greater distances throughout the tissue or tumor.

The applicant has surprisingly found that portable pumps, so far not accepted to be usable for convection enhanced delivery techniques because of their discontinuous flow characteristics, can be applied for convection enhanced delivery technique in combination with at least one infiltration catheter of the present invention. The portable pump enables for the first time out-patient treatment with convection enhanced delivery technique. Further using a access port system comprising a access port chamber with a access port catheter and an infusing tube with a access port needle, the advances of access port system technology additionally are accessible with the device for convection enhanced delivery administration.

Figure 2:
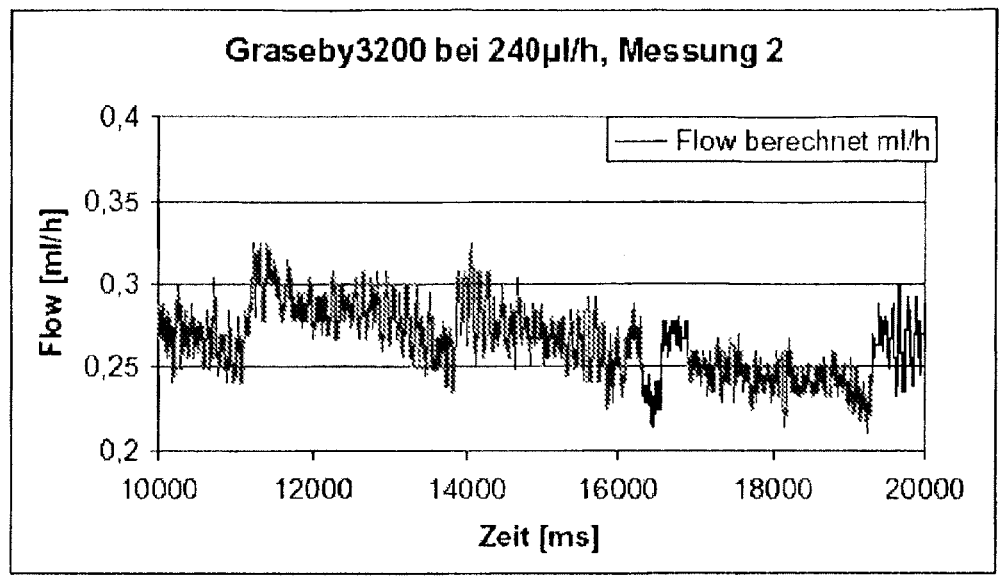
FIGS. 2a and b depict the flow characteristics of a syringe pump ("Graseby® 3200", Fa. AxMediTec) often used in clinics for convection enhanced delivery application.
FIG. 2b shows the flow characteristic of that pump at a set flow of 480 µL/h.
Figure 2:
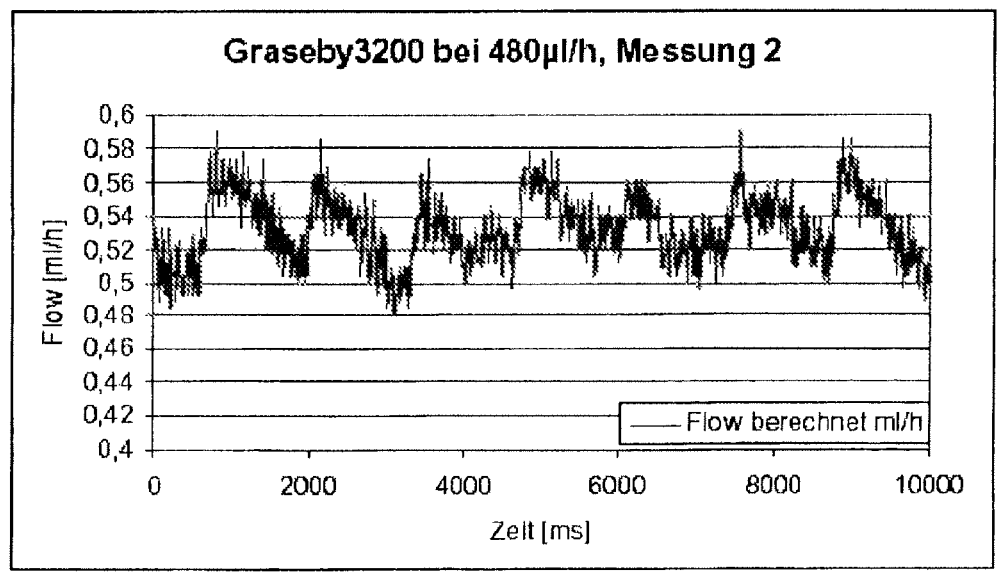

Before the present invention, clinically useful constant flows rates used in conjunction with convection enhanced delivery could only be achieved with syringe pumps, such as, for example, a Graseby® 3200 or a Harvard® 2100. These syringe pumps are typically connected directly to an infusion catheter or connected by an infusion tube implanted into a tissue such as brain tissue, as described in the international publication WO 95/05864. The maximal oscillation of these syringe pumps when used in combination with an infusing tube, an access port, an access port catheter and a filter was as low as about 0.05 mL/h and a oscillation with a frequency of about 0.7 $sec^{-1}$ at a set flow rate of 0.48 mL/h as shown in FIG. 2b.

The flow characteristic of various portable pumps delivered in steps of about 0.05 mL to about 0.1 mL even in continuous flow mode, thus providing high oscillations of the actual flow. This high oscillation value is not optimal for use with convection enhanced delivery in many tissues, particularly, for example, into brain tissue where constant flow rates of 0.1 µL/min to 15.0 µL/min are desired. One device claiming to deliver at minimal steps of 0.4 µL in the continuous flow mode was tested by the applicants. Since it is known that tubing and other devices may smoothen the flow characteristic applicants connected an infusion tubing, an access port with an access port catheter and a further infiltration catheter to the pump and recorded the flow characteristic. Despite of the smoothing influence of the device the portable pumps showed a flow characteristic with a 20 fold higher oscillation than those shown by comparator syringe pumps (FIGS. 2a and 2b) in the same test setting.

Figure 3:
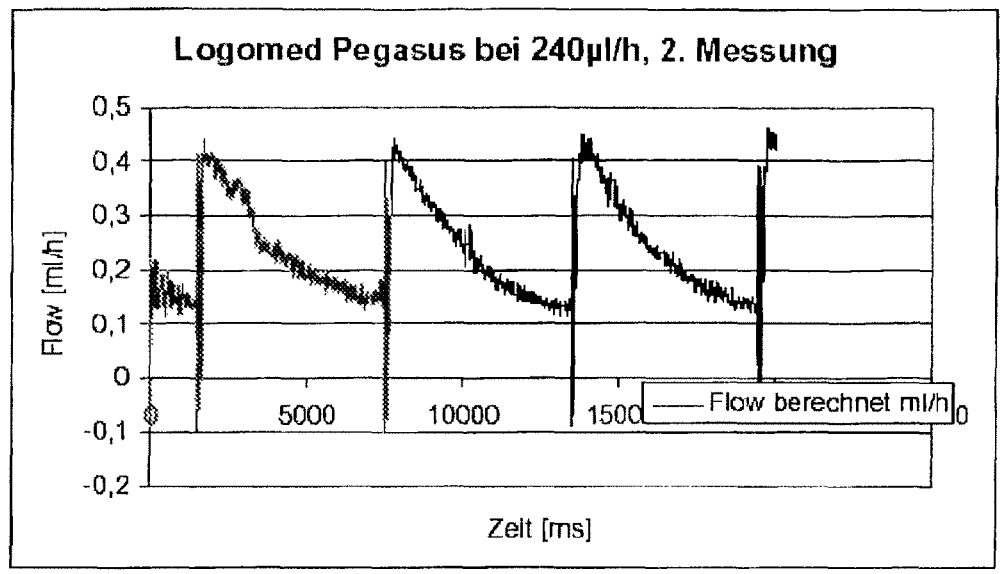
FIGS. 3a and 3b depict the flow characteristic of a Portable Pump ("Pegasus Vario" from the company LogoMed).
Figure 3:
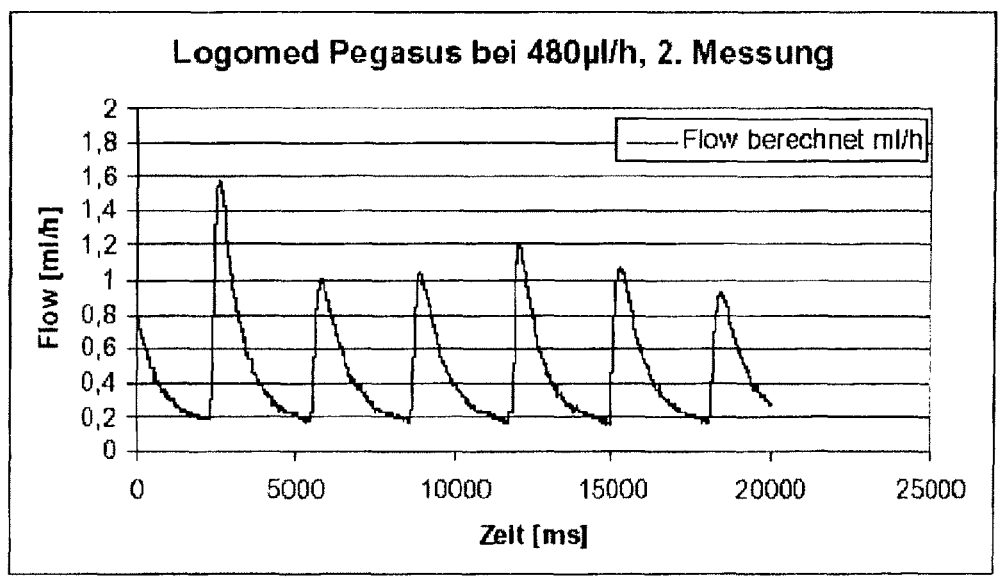

The flow characteristics of the portable pump under test ("Pegasus Vario, Fa. Logomed) at a set flow of 480 µL/h showing an oscillation of up to 1 mL/h with a frequency of 0.3 $sec^{-1}$ is depicted in FIG. 3b. The flow characteristics were recorded using a specific "liquid flow" measurement system at Institut für Mikro- and Informationstechnik, Villingen Schwenningen, Germany. The measurement compares the flow of the tested system with a reference flow using calibrated sensors of the company Bronkhorst applying hydrostatic technique (SP45, type: 300×600tp45). Details of the experiment are described in Example 3.

Surprisingly, applicants found that this rough flow characteristic of the portable pump (Pegasus Vario, Fa. Logomed) was still suitable for the convection enhanced delivery when used in conjunction with the present invention. The completed experiment carried out to demonstrate the suitability for convection enhanced delivery technique of the pump showing the flow characteristic is described in Example 1.

In one embodiment of the present invention, the device induces a flow continuously higher than about 0.001 mL/h and in average lower than about 0.5 mL/h is appropriate for convection enhanced delivery in brain tissue if the total flow volume within one period of the oscillation is less than about 0.5 µL and the amplitude of the oscillation is between about 0.1 mL/h and about 0.8 mL/h.

Also desired for patient compliance is the cosmetic advantages of an infusing system in a case where the target for the administered substance is beyond a visible part of the body (for example, brain tissue) where according to the state of art in convection enhanced delivery application systems, the infusion catheter was hanging from the head of the subject at the point of insertion.

Rinsing the perfusion holes of a catheter implanted into a tissue or tumor with a constant flow, as well as a periodical flow, prevents the perfusion holes of the infusion from overgrowth with cells, especially from, for example, quickly growing tumor cells, when the infusion catheter is placed in tumor or tissue. Overgrowth is believed to happen rapidly as soon as no solvent is administered over a period of several hours to days resulting in a blockage of the device. Thus administration of substances directly into tissue (apart from body fluids or cavities) at repeated cycles with treatment-free intervals as well as during long term administration become possible with the device according to the present invention. Additional surgeries for implanting the infusion catheter connected with the danger of contamination and the resulting infections necessary according to the state of the art thus are avoided as well. The flows necessary to keep the perfusion holes open depends on several factors including, for example, the number of perfusion holes, their diameter and the rapidity of tumor cell growth. In one embodiment, the flow to prevent such overgrowth varies between about 0.001 mL/h to about 1 mL/h final flow in the infusion catheter.

The fluid pharmaceutical agent suitable for use in the present invention include any agent suitable for delivery in a solvent system, or, for example, formulated for delivery in an aqueous solution, such as for subcutaneous injection. Such pharmaceutical agents include, for example, analgetics, agents for the treatment of wounds, analeptics, anaesthetics, anthelmintics, anticoagulatives, antirheumatics, antiallergics, antiarrhythmics, antibiotics, antidementiva, antidiabetica, antidotes, antiepileptics, antihemorrhagics, antihypertonics, antihypnotics, anti migrain preparation, antimycotics, antineoplasics, anti-parcinson agent, antiphlogistics, anti-sense oligonucleotides, antituberculosis drugs, anti-arteriosclerotic agents, biologic materials, blood flow stimulants, cholagogas, corticoids, cytokines, cytostatics, diagnostics, fibrinolytics, geriatrics, gonadotropins, hepatics, hormones and their inhibitors, hypnotics, immunglobulines, immunomudulators, immunotherapeutics, organ perfusion solvents, proteins, protein toxins, protectives, sedatives, cardiac remedys, depressants and stimulants, minerals, muscle relaxants, neurotropic agents, oligonucleotides, ophthalmics, osteoporotic agents, otologics, psychopharmaceuticals, sera, thyroid preparations, vaccines, spasmolytics, urologics, vitamins, drugs, proteins, protein toxins, antibodies for treatment, proteins in enzyme replacement therapy, growth factors, vectors, viruses in gene therapy and/or agents for diagnosis as agents or antibodies for imaging, x-ray contrasting mediums, oligonucleotides inhibiting the expression of, for example, TGF-β, MIA, c-erbB-2/HER-2, or IL-10, and/or combinations thereof. The active substances may be dissolved or suspended in a physiological solvent or in any other appropriate solvent. The above agents may in the form of a free base, or a salt, hydrate, ester, amide, enantiomer, isomer, tautomer, polymorph, prodrug, or derivative of these compounds. (Based in part upon the list provided in *The Merck Index*, Merck & Co. Rahway, N.J. (2001)). The above mentioned agents as well as combinations thereof can be used in the apparatuses, methods, kits, combinations, and compositions herein described.

In one embodiment of the present invention, the surface of the apparatus in contact with the therapeutic agent may be coated in appropriate manner. Illustratively, the coating can be an antiinfective, an antiviral, a fungicide, or a X-ray absorbing material. Furthermore the surface can be modified by surface modifying groups in a way that blood compatibility, abrasion resistance, coefficient of friction and resistance to degradation or molecular adhesion are reduced.

In one embodiment, the flexible tubes are connected by a pipe or tube with an outer and an inner diameter, with the outer diameter having a slightly greater diameter than the inner diameter of the tube that is connected by this pipe preventing the solvent of the tube from escaping. In yet another embodiment, the outer diameter of the pipe or tube has a radial deepening or heightening to improve the seat of the tube on the pipe or tube. Squeezing the tube from the exterior to the connecting pipe the seat of the tube can further improve the connection.

The components of a device of the present invention can be fabricated from a range of materials including, for example, a metallic, a polymeric, and/or a composite material, including materials such as titanium, high grade steal, aluminium, alloys, polymeric foams, plastics, stainless steel and/or metal, and combinations, mixtures, and modification thereof. Materials intended for implantation into a subject can be made of biocompatible materials, such as, for example, polymers, polymeric segments of polystyrene, polyolefins, polyamides, or polyurethane, and metals. Selection of such materials depends on a number of factors including the mechanical properties desired, and the porosity, surface properties, and toxicity of the material. Illustratively, a component of the present invention can be made of titanium, an alloy, stainless steel, a ceramic, silicon, Teflon®, polypropylene, polyethylene, polystyrene, polyolefins, polyimide, polyamides, polyurethane, PET, PETG, PETE, PE, PTG, HDPE, PC, PVC, nylon, urethane, and/or a co-polymer, for example, and may be laminated with or otherwise include a layer of gold, silver and/or aluminum (to minimize permeability to gas and liquids) sputtered or otherwise deposited or incorporated therein. Some commercially available products useful in fabricating the present invention include, for example, BioSpan® segmented polyurethaneurea, Bionate® polycarbonate urethane, Elasthane™, and Elasthane™ polyetherurethane, which can be used in chronically-implanted medical devices. Elasthane™ has a chemical structure and properties similar to Pellethane® 2363. Thermoplastic silicone-urethane co-polymers such as PurSil™ silicone polyetherurethane and CarboSil™ silicone polycarbonate urethane can also be used in the present invention.

In yet another embodiment, the connecting device is a screw connection. Illustratively, the thread on one port fits a nut on another port such that fluid communication is possible. In one embodiment, between the two ports there is a seal which is self-sealing to prevent solvent from leaking. In yet another embodiment, the nut of one port contains a locking system. Illustratively, a locking system is an eye attached to a nut and several eyes at the counterpart port that allows easily fixing the screw connection by a wire, nail, screw, stitch, etc. In yet another embodiment, the connecting system is a bayonet joint comprising two counterpart ports. The ports can be self-sealing. Bayonet joint includes integrated locking systems. Many other technique according to the state of the art can be applied in connecting ports of the present invention.

In one embodiment of the present invention, the apparatus contains a distributor, which in one embodiment can be a device containing a number of proximal ports equivalent to the number of infusion catheters are to be connected, a distal port, and a lumen therethrough. Illustratively, the distributor is indwelling and is made from a solid material, such as, for example, a polymeric material, a plastic, and/or a metal. In one embodiment, the distributor has appropriate connectors and locking systems for establishing permanent fluid communication with the access port catheter and the infusion catheter. The diameter of the distal port and the accessory lumen in one embodiment, is large enough to support all proximal ports with their accessory lumens with equivalent flow of the solvent. In one embodiment of the present invention, the equivalent diameters of the proximal ports are less than the diameter of the distal port. In yet another embodiment, the diameters of the different proximal ports differ from each other correlating to the type of infiltration catheter connected herewith (inner diameter of the infusion catheter, number of infusion holes, diameter of these holes etc.).

Within the low connection between the infusion catheter and the means for injection, a filter system may be integrated into the apparatus at any appropriate location. Illustratively, the filter system comprises a sterile filter for removing pathogens; a biological filer for biological materials such as proteins and/or antibodies; a particle filter for removing particulates; a chemical filter for removing chemicals; and/or a filter for removing air or gasses from the solvent. In one embodiment, each filter has a distal port and a proximal port and a lumen therethrough. Within the lumen of each filter there is a membrane or any other appropriate device for removing air, particles, chemicals, and/or biological materials, such as, for example, pathogens including bacteria, fungi, and/or viruses. The different filter types are known to those skilled in the art, and can have separate casings, or have common casings. In one embodiment, the filter for removing air is placed extra corporal. In yet another embodiment, the filter for removing particles is positioned upstream the sterile filter. The sterile filter is typically characterised by a pore diameter of about 0.45 μm or less, or about 0.22 μm or less, or about 0.1 μm or less. The particle filter is characterized having a pore diameter of greater than about 0.45 μm, or greater than about 0.22 μm. In yet another embodiment, the filters are placed in a sequence, from upstream to downstream, of air filter, particle filter and sterile filter. In yet another embodiment of the present invention, the filters are placed extra corporal, and have a flat profile that can be easily fixed on the skin. In yet another embodiment all filters are located outside the body, which facilitates maintenance and replacement. One or more filters of the same or different category can be used in one embodiment of the device.

In one embodiment, the infusion catheter has an elongated body with a proximal port (see, for example, FIG. 7, 9a), a distal port (see, for example, FIG. 7, 9c), and an interior lumen therethrough and perfusion holes. The lumen of the infusion catheter can be separated into several lumens.

In yet another embodiment of the present invention, the perfusion holes are in an area near to the proximal end of the infusion catheter. Illustratively, the infusion catheter material can be an inert material, a pliable material, and/or a biocompatible polymer, such as, for example, a polymeric material, a plastic, and/or a metal, including, polypropylene, polyethylene, polyimide, polyamid, polyurethane, and/or silicon.

In another embodiment of the present invention, the infusion catheter may be stabilized with, or impregnated with a wire, to facilitate or act as a detectable marker that allows for monitoring the position of the infusion catheter (for example, a barium compound in case of x-ray monitoring). The detectable marker can be restricted to the proximal end of the infusion catheter, and/or have scaling marks placed at regular intervals over the catheter.

Illustratively, the lumen of the catheter may be cylindrical, oval or angular and have one, two, three, or four or more lumens. The catheter can have perfusion holes in any appropriate form, number, diameter and location depending on the tissue or tumor that is to be infiltrated. The perfusion holes may be positioned for example, oppositely, radially, helically, symmetrically and/or asymmetrically around the axis of the infusion catheter. The proximal end of the infusion catheter may be sharp, obtuse, or round depending of the consistency of the tissue into which the infusion catheter is to be implanted.

In yet another embodiment of the present invention, the perfusion hole can come into existence by simply cutting off the proximal end of the catheter. The catheter may be stabilized with a removable stylet made of any appropriate material (for example, a polymeric material, a plastic, and/or a metal) stable enough to place the infusion catheter in the tissue or tumor and being removed after the catheter is at its appropriate location within the tissue or tumor.

In another embodiment, the infusion catheter has an additional device for its fixation to a disc mesh, and/or a suture flange. In one embodiment, the fixture has hole in the diameter of the catheter and one or even more additional holes of appropriate diameter, that allows it to affix the fixture with the catheter by a nail, screw, stitch, etc., to a solid tissue or bone. In yet another embodiment, the infusion catheter has retention beads in any appropriate area.

For establishing fluid communication between corresponding ports of the embodiments described herein (for example, a reservoir, a pump, an access port, and/or infusion tube) a tube with two ports of any length and a proximal and a distal port can be integrated into the device. The diameter of this tube has to be appropriate considering the flow, the volume of the solvent that has to be injected. A tube might have a length to up about 1.5 m and a diameter from about 0.1 mm to about 5 mm. The material of the tube can be in one embodiment a flexible polymer. The infusion tube has a proximal port and a distal port and a lumen therethrough.

In one embodiment of the present invention, one or more of the indwelling parts and/or one or more of the parts that are in contact with the fluid pharmaceutical agent and/or the physiological solution are of materials that are physiologically compatible, and include, for example, titanium, high grade steal, surface treated aluminium and their alloys, ceramics, polymers such as polypropylene, polyurethane, polyethylene, polyimide, polyamide, silicon, Teflon®, and combinations, mixtures, and modification thereof.

In one embodiment of the present invention, the means for injecting a solvent has a proximal port and has a distal port or distal end and a lumen therethrough. Means for injection comprises, for example, syringes, balloons, pumps or other device appropriate for infusing a certain amount of solvents once or several times with constant, increasing and/or decreasing flow as well as combinations thereof.

In one embodiment of the present invention, the one way valve has a distal port and a proximal port and a lumen therethrough. The one way valve comprises a device enabling the flow of a solvent only into one direction. If the flow is in the other direction the valve is in a closed position. The mechanism of the one way valve can be any mechanism known to those skilled in the art, and can be based on, for example, spheres, membranes, lamellars, etc. The valves are integrated into the apparatuses at any appropriate place to provide the appropriate functionality desired. Illustratively, the one way valves comprises connecting and/or locking devices at their distal and proximal port.

In one embodiment of the present invention, the portable pump is a gas pressure pump, piston pump, radial piston pump, membrane pump, syringe pump, centrifugal pump, suction pump, or any other mechanism inducing a flow characteristic according to the present invention. In yet another embodiment of the present invention, the flow characteristic of the pump is enhanced by an expanding volume that is in fluid communication with the lumen of the port downstream the pump mechanism. In one embodiment, the expanding volume is a soft tube with a closed distal end and an open proximal end and a lumen therethrough. This tube is in fluid communication with the solvent coming from the pump. The volume is expanding during the time the pump feeds the solvent and the lumen is contracting during the interval the pump feeds no solvent thus smoothing the peaks of the flow.

In one embodiment of the present invention, the access port system comprises an accessory system, an access port casing and an access port catheter. The access port chamber has a distal end and a proximal port and a lumen therethrough. The access port catheter as well has a distal end and a proximal end and a lumen therethrough. The access port chamber can be any commercially available access port system made of rigid biocompatible material, including, for example, a metallic, a polymeric, and/or a composite material. In one embodiment the access port chamber has appropriate devices for its fixation such as eyes for nails, suture, screws or hooks etc. Illustratively, the access port has one or more chambers.

In another embodiment of the present invention, the proximal port of the access port chamber is in fluid communication with the distal port of the access port catheter. As depicted in FIG. 6, the outlet of the access port chamber is a pipe (see FIG. 6, 6c). In yet another embodiment, this pipe has at least one heightening or deepening that improves, in combination with an appropriate locking system, the connection between the access port chamber and the access port catheter.

The access port catheter is from any pliable biocompatible material, including, for example, a metallic, a polymeric, and/or a composite materials. The access port catheter can be stabilized with a wire or any comparable technique for improving its implanting. The wire can be removable. The catheter can be impregnated or contain a detectable marker that allows to monitor the position of the catheter (for example, barium compounds in case of x-ray monitoring).

The access port casing and the access port catheter are implanted subcutaneously. The accessory system is any device that enables fluid communication between the extracorporal infusion tube and/or means for injection and the subcutaneously implanted access port chamber.

In one embodiment where using an access port needle as an accessory system the distal end of the access port chamber and is covered with a septum made of resilient and pliable material such as silicon rubber that is self sealing even if a needle is pricked through the septum several times. Any other technique for the accessory system allowing a repeated injection into the access port chamber may be used.

In yet another embodiment the access port system comprises two or more of the above mentioned access port chambers. In one embodiment these two access port chambers are integrated into one casing next to each other and have the same structure as described for an access port system with a single access port chamber. One access port chamber is optionally covered with a needle screen. In yet another embodiment the two access port chambers are beyond each other. Both access port chambers can also have a septum. The proximal access port chamber has a smaller septum integrated to the bottom of the distal chamber and additionally covered with a needle screen. Each access port chamber has its own proximal port in fluid communication with the distal port of the access port catheter.

In one embodiment of the present invention, the access port needle has a distal port and a proximal port and a lumen therethrough. The access port needle in one embodiment is stable and long enough to connect the proximal port of the infusing tube with the distal end of the access port chamber, after the access port chamber is implanted subcutaneously. In one embodiment the tip of the needle is bevelled to prevent the silicon septum of the access port chamber from rupturing. Illustratively, the needle is straight or angled at between about 1° to about 180°, or at about 1°, or about 15°, or about 30°, or about 45°, of about 60°, or about 90°, or about 120°, or about 150°, or about 180°. In another embodiment, the needle is covered with a transparent top, lined with a soft, non-irritant material that prevents the surrounding of the injection site from contamination.

The solvent reservoir is any device having a proximal port and a distal port or distal end and a lumen therethrough. In one embodiment of the present invention, the lumen is large enough to support the pump for several days at a flow rate leading to a final flow in the infusion catheter of about 0.001 µL/h up to about 1 mL/h. In one embodiment the reservoir comprises two transparent cling films fit together at their border creating a receptacle with a flexible lumen. In one corner of the receptacle a tube is integrated having a proximal port, a distal port and a lumen therethrough. The lumen of this tube is in fluid communication with the lumen of the receptacle.

In one embodiment of the present invention, the reservoir is integrated into the casing of a portable pump. In yet another embodiment the size of the portable pump including the integrated reservoir is not larger than about 125 cm$^3$, 250 cm$^3$, 500 cm$^3$, 750 cm$^3$, 1,000 cm$^3$, 1,250 cm$^3$, 1,500 cm$^3$, or 3,000 cm$^3$. Illustratively, the reservoir is no larger than about 10 cm×15 cm×5 cm.

The materials and/or the construction respectively of all tubes, the reservoir, the catheters, access ports, filters and the pump can be such that the flow characteristic is not negatively influenced by movements as described under definitions "Portable Pump" and usual operations with the apparatuses.

All implanted devices, as well as devices in contact with the solvent determined to be infused can be fabricated of material compatible with sterilization, including, for example, chemical, steam, and/or radiation sterilization, and can be sterile before use.

Illustratively, the apparatus of the present invention can be implanted into a tumor where a solvent deliverable anti-tumor agent is indicated. Such tumors include, for example, a blastoma, breast cancer, esophageal cancer, head and neck cancer, ovarian cancer, sarcoma (including, osteosarcoma and chondrosarcoma), small-cell bronchogenic/lung carcinoma, non-small-cell bronchogenic/lung carcinoma, colon carcinoma, colorectal carcinoma, gastric cancer, small intestine carcinoma, liver carcinoma, carcinoma of the kidney, pancreas carcinoma, gallbladder cancer, cervical carcinoma, endometrial cancer, mesothelioma, prostate carcinoma, testicular carcinoma, brain tumor, non-Hodgkins lymphoma, Hodgkins-lymphoma, and/or a solid neoplasm.

The target tissue may include any tissue of the subject where treatment with a solvent deliverable therapeutic agent is indicated. Such tissues include brain, bone marrow, bone, joints, thyroid, gall, heart, lung, muscle, spleen, kidney, liver, prostate, pancreas, stomach, vein and artery tissue.

Besides being useful in human treatment, the present invention is also useful for other subjects including veterinary animals, reptiles, birds, exotic animals and farm animals, including mammals, rodents, and the like. Mammals include horses, dogs, pigs, cats, or primates (for example, a monkey, a chimpanzee, or a lemur). Rodents includes rats, mice, squirrels, or guinea pigs.

One embodiment of an apparatus for delivering a solvent to a tissue or a tumor according to the present invention comprises a means for injecting a solvent having a proximal port in fluid communication with a distal port of at least one infusion catheter, which is operatively implanted with its proximal end into a tissue or tumor. In one embodiment, the two ports are fixed by a connecting and/or locking device.

In another embodiment, the apparatus may further comprise an infusing tube establishing fluid communication between the proximal port of the means for infusing a solvent and the distal port of the infusion catheter. In yet another embodiment, the device may additionally have integrated a filter system, one way valves inhibiting the proximal distal reflux and/or additional tubes.

Yet another embodiment of an apparatus for delivering a solvent to a tissue or a tumor according to this invention comprises two or more infusion catheters to improve the infiltration of the solvent into the tissue and/or tumor.

In one embodiment, the apparatus can further comprise a distributor with a number of proximal ports equivalent to the number of infusion catheters, a distal port and a lumen therethrough.

The device of the present invention may additionally have an integrated filter system, one way valves and/or additional tubes.

In yet another embodiment of apparatuses for delivering a solvent to a tissue or a tumor according to this invention the means for injecting a solvent comprises a portable pump. The proximal port of the pump is in fluid communication with the distal port of at least one infusion catheter. The distal port of the portable pump is in fluid communication with the proximal port of a solvent reservoir. In one embodiment, the device may further comprise an additional infusing tube establishing the fluid communication between the proximal port of the portable pump and the distal port of the infusion catheter.

In yet another embodiment of the present invention, an apparatus for delivering a solvent to a tissue or a tumor comprises a means for injecting a solvent with the proximal port in fluid communication with the distal port of an infusion tube. The proximal port of the infusion tube is in fluid communication with the distal portion of an access port chamber via an accessory system. The access port chamber is subcutaneously implanted, for example, over a rib. The proximal port of the access port chamber is in fluid communication with the distal port of the access port catheter and the proximal port of the access port catheter is in fluid communication with the distal port of at least one infusion catheter. Several catheters might be in fluid communication with the proximal port of the access port catheter by an additional distributor. The proximal end of the infusion catheter is operatively implanted into the target tissue or tumor. In yet another embodiment of the present invention, the means for injecting a solvent and the infusing tube are outside the body. All ports can be connected with appropriate connecting and locking device.

In one embodiment, the access port chamber, the access port catheter and/or the infusion catheter are indwelling.

In yet another embodiment, the pump with a reservoir and the infusing tube are outside the body.

Yet another embodiment of apparatuses for delivering a solvent to a tissue or a tumor comprises a pump or a portable pump for injecting a solvent connected with its distal port to a reservoir or a syringe pump being filled with an appropriate amount of solvent for infusing the target tissue or tumor for several minutes, hours, days or weeks. The proximal port of the pump is in fluid communication with the distal port of an infusion tube. The proximal port of the infusion tube is in fluid communication with the distal part of an access port chamber by an accessory system. The proximal port of the access port chamber is in fluid communication with the access port catheter and the proximal port of the access port catheter is in fluid communication with the distal port of at least one infusion catheter. Also several catheters might be in fluid communication with the proximal port of the access port catheter by an additional distributor. The proximal end of the infusion catheter is operatively implanted into the target tissue or tumor. All ports can be connected with appropriate connecting and locking device.

In yet another embodiment of the present invention, the apparatuses further comprises a ventricular shunt. The ventricular shunt can comprise a tube of appropriate diameter that has a proximal end surgically implanted into the intraspinal liquid and a distal port and a lumen therethrough. The distal port of this shunt is in fluid communication with a body cavity, for example, a vein, an intraperitoneal space or a distal port of a access port system. In yet another embodiment the ventricular shunt comprises at least one catheter with its openings ending in the intraspinal fluid a distal port and a lumen therethrough. This catheter can be elongated by further tubes as well as one-way valves might be integrated. All parts can be connected by appropriate connecting and/or locking device.

In yet another embodiment, the proximal port of the access port catheter is in fluid communication with the distal port of a distributor. The distal ports of two or more infusion catheters are in fluid communication with the equivalent number of proximal ports of the distributor. In one embodiment, the ventricular shunt may additionally have one or more integrated one-way valves, an additional tube, and can be connected by appropriate connecting and locking device.

In yet another embodiment of the present invention, the apparatus comprises two access ports. The proximal port of one of the indwelling access ports is in fluid communication via the access port catheter and appropriate connectors and locking systems with the distal port of at least one infusion catheter surgically implanted into a tumor or tissue. The distal port of this access port is in fluid communication with a means for injection a fluid solvent. Further infusion tubes, filter systems, accessory systems etc., may be integrated into this apparatus as described in the embodiments above. The proximal port of the second access port chamber can be in fluid communication with the distal port of a second access port catheter. In one embodiment, the proximal port of the access port catheter is in fluid communication with the ventricular shunt. In yet another embodiment, the distal end of the second access port chamber is covered by a septum allowing repeated pricking with an access port needle and removing intraspinal liquid for diagnostic and/or therapeutic reasons by means for removing a solvent.

The means for moving a solvent can be any device such as for example, a solvent reservoir, a syringe or a balloon. Additional tubes, valves or flow regulators can be integrated into the device. In one embodiment the distal port of the access port needle is in fluid communication with a tube having a distal port and a proximal port and a lumen therethrough. The distal port of the tube is in flow communication with the proximal port of a portable pump removing liquid from the intrathecal lumen. The flow of removing intrathecal fluid in one embodiment is up to the flow the fluid pharmaceutical agent or the physiological solvent is administered into the tissue or tumor.

The diameters and length of all tubing, catheters connectors and ports of the apparatuses described in this application can have an appropriate scope corresponding to the flow rate.

Yet another embodiment of this invention comprises one of the embodiments described above wherein at least one of the lumens in contact with the solvent and/or the indwelling parts is sterile.

Yet another embodiment of this invention comprises any of the embodiments described above filled with a solvent that is selected from the physiological solvent and/or a fluid pharmaceutical agent.

Yet another embodiment of this invention is the use of one of the apparatuses described herein for administering the solvent to a target tissue or tumor applying convection enhanced delivery, which is also named high pressure microperfusion. This generally means that the delivery of a solvent induces a bulk flow current in the target tissue or tumor that has the potential to homogeneously distribute even large molecules throughout a tissue or tumor. The flow of the solvent depends on the specific tissue or tumor the fluid pharmaceutical agent is administered to and in some cases might be even higher than the ranges given here.

In inducing a bulk flow current in brain tissue, in one embodiment of the present invention, a continuous flow of a fluid pharmaceutical agent of about 0.001 mL/h up to about 1 mL/h is infused, or about 0.1 mL/h up to about 0.8 mL/h, or about 0.2 mL/h, or about 0.5 mL/h is infused.

In yet another embodiment of the present invention, the flow induced by a pump meets at least on of the following flow characteristics in at least one of the infusion catheters: an average flow of between about 0.001 mL/h or about 1.0 mL/h; a total flow volume within one period of any oscillation of less than about 0.5 µl; and/or an amplitude of the oscillation between about 0.1 mL/h and about 1 mL/h.

In yet another embodiment of the present invention an apparatus that induces a flow in the infusion catheter as described herein applies constant average flows, increasing or decreasing flows as well as combinations thereof.

In yet another embodiment of the present invention, the apparatus is used for interval therapy, meaning that the fluid pharmaceutical agent is administered alternating with another fluid pharmaceutical agent and/or a physiological solvent. The flow of the physiological solvent during the time no other fluid pharmaceutical agent is administered depends on many factors including, for example, the target tissue. Illustratively, for convection enhanced delivery in brain tissue the flow can vary between about 0.001 mL/h to about 1 mL/h, or between about 0.01 mL/h to about 0.4 mL/h, or between about 0.05 mL to about 0.3 mL/h in each infusion catheter. The pump in one embodiment also works periodically using increasing or decreasing flows, as well as combinations thereof.

In yet another embodiment, the infusion catheter is surgically implanted with its perfusion holes terminating in the tumor or tissue in which the fluid pharmaceutical agent is being administered to. The access port chamber connected with the access port catheter is implanted at any appropriate location. In one embodiment, the access port catheter is tunneled towards the open end of the infusion catheter. The access port catheter as well as the infusion catheter can be shortened to an appropriate length, considering that they are laid slack enough to follow movements of the body without influencing the exact position nor of the infusion catheter neither of the access port. Finally the access port catheter is connected with the infusion catheter by an appropriate connector. In yet another embodiment, the implanted device is filled with a physiological solution in which the fluid pharmaceutical agent is to be infused with.

Even if the description is focused on tumors and tissues, the method of this invention can be used for body cavities, veins and arteries as well.

In yet another embodiment, the pump is portable and has a fluid reservoir large enough to support convection enhanced delivery for several days at a flow rate leading to a final flow in the infusion catheter between 0.1 and 15 µL/min, or between 2 and 12 µL/min, or between 3 and 10 µL/min.

Up to now, to get a constant flow only syringe pumps such as the commonly used "Graseby® 3200" syringe pump were clinically used for convection enhanced delivery treatment for reasons of their constant flow characteristic. In one embodiment, the maximal oscillation of such a syringe in combination with an infusing tube, a access port, a access port catheter and a filter is as low as 0.1 mL/h within one second around the average flow rate of 480 µL/min as shown in FIG. 2b.

In one embodiment, a pump showing a flow characteristic of an oscillation of 1 mL/h, or greater, within a second in combination with a catheter is appropriate for convection enhanced delivery technique.

In one embodiment of the present invention, the compounds administered to the subject are formulated as an injectable formulation and comprise, for example, an aqueous solution or suspension of the compounds suitable for intravenous delivery. When preparing the composition for injection, particularly for intravenous delivery, illustratively, the continuous phase comprises an aqueous solution of tonicity modifiers, buffered to a pH below 7, for example, or below 6, for example. The tonicity modifiers comprise, for example, sodium chloride, glucose, mannitol, trehalose, glycerol, or other pharmaceutical agents that renders the osmotic pressure of the formulation isotonic with blood. Alternatively, when a larger quantity of the tonicity modifier is used in the formulation, it can be diluted prior to injection with a pharmaceutically acceptable diluent to render the mixture isotonic with blood.

In another embodiment of the present invention, a preservative is added to the formulation. Illustratively, a preservative includes benzalkonium chloride, propylparabem, butylparaben, chlorobutanol, benzyl alcohol, phenol, sodium benzoate, or EDTA.

The compositions of the present invention can further comprise a pharmaceutically acceptable carrier. The carrier materials that can be employed in making the compositions of the present invention are any of those commonly used excipients in pharmaceutics and should be selected on the basis of compatibility with the pharmaceutical agent and the release profile properties of the desired dosage form. Illustratively, a pharmaceutical excipient except active drugs are chosen below as examples:

(a) Binders such as acacia, alginic acid and salts thereof, cellulose derivatives, methylcellulose, hydroxyethyl cellulose, hydroxypropyl cellulose, magnesium aluminum silicate, polyethylene glycol, gums, polysaccharide acids, bentonites, hydroxypropyl methylcellulose, gelatin, polyvinylpyrrolidone, polyvinylpyrrolidone/vinyl acetate copolymer, crospovidone, povidone, polymethacrylates, hydroxypropylmethylcellulose, hydroxypropylcellulose, starch, pregelatinized starch, ethylcellulose, tragacanth, dextrin, microcrystalline cellulose, sucrose, or glucose, and the like.

(b) Disintegration agents such as starches, pregelatinized corn starch, pregelatinized starch, celluloses, cross-linked carboxymethylcellulose, sodium starch glycolate, crospovidone, cross-linked polyvinylpyrrolidone, croscarmellose sodium, a calcium, a sodium alginate complex, clays, alginates, gums, or sodium starch glycolate, and any disintegration agents used in tablet preparations.

(c) Filling agents such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

(d) Surfactants such as sodium lauryl sulfate, sorbitan monooleate, polyoxyethylene sorbitan monooleate, polysorbates, polaxomers, bile salts, glyceryl monostearate, Pluronic™ line (BASF), and the like.

(e) Solubilizer such as citric acid, succinic acid, fumaric acid, malic acid, tartaric acid, maleic acid, glutaric acid sodium bicarbonate and sodium carbonate and the like.

(f) Stabilizers such as any antioxidation agents, buffers, or acids, and the like, can also be utilized.

(g) Lubricants such as magnesium stearate, calcium hydroxide, talc, sodium stearyl fumarate, hydrogenated vegetable oil, stearic acid, glyceryl behapate, magnesium, calcium and sodium stearates, stearic acid, talc, waxes, Stearowet, boric acid, sodium benzoate, sodium acetate, sodium chloride, DL-leucine, polyethylene glycols, sodium oleate, or sodium lauryl sulfate, and the like.

(h) Wetting agents such as oleic acid, glyceryl monostearate, sorbitan monooleate, sorbitan monolaurate, triethanolamine oleate, polyoxyethylene sorbitan monooleate, polyoxyethylene sorbitan monolaurate, sodium oleate, or sodium lauryl sulfate, and the like.

(i) Diluents such lactose, starch, mannitol, sorbitol, dextrose, microcrystalline cellulose, dibasic calcium phosphate, sucrose-based diluents, confectioner's sugar, monobasic calcium sulfate monohydrate, calcium sulfate dihydrate, calcium lactate trihydrate, dextrates, inositol, hydrolyzed cereal solids, amylose, powdered cellulose, calcium carbonate, glycine, or bentonite, and the like.

(j) Anti-adherents or glidants such as talc, corn starch, DL-leucine, sodium lauryl sulfate, and magnesium, calcium, or sodium stearates, and the like.

(k) Pharmaceutically compatible carrier comprises acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate, carrageenan, monoglyceride, diglyceride, or pregelatinized starch, and the like.

Additionally, drug formulations are discussed in, for example, Hoover, John E., *Remington's Pharmaceutical Sciences*, Mack Publishing Co., Easton, Pa. 1975. Another discussion of drug formulations can be found in Liberman, H. A. and Lachman, L., Eds., *Pharmaceutical Dosage Forms*, Marcel Decker, New York, N.Y., 1980.

The phrase "accessory system" refers to a device enabling fluid access into an access port.

The term "connector" refers to a device used for connecting tubes, catheters, reservoirs, pumps, access ports that are in fluid communication in a way that the fluid communication is given and the fluid communication is prevented from disconnection by mechanical strain.

The phrase "convection enhanced delivery" refers to delivery of a solvent inducing a bulk flow current into a target tissue or tumor that has the potential to homogeneously distribute even large molecules through long distances throughout the tissue or tumor. This is also known as high pressure microperfusion.

The term "distal" refers to that part of the device that is upstream in the flow direction when viewed from the tumor or tissue into which the infusion catheter is implanted.

The phrase "expanding volume" refers to any flexible device or apparatus downstream the pump additionally integrated into the tubing for smoothing the peaks of the flow induced by the pump. The casing of the expanding volume therefore has to be flexible enough to compensate flow peaks/pressure peaks respectively. The lumen of the expanding volume is expanding during the time the pump feeds the solvent and the lumen is contracting during the interval the pump feeds no solvent, therefore, smoothing the peaks of the downstream flow of the device.

The expanding volume can be, for example, a balloon, a membrane, a soft tube etc.

The phrase "fluid pharmaceutical agent" refers to a fluid containing a pharmaceutical substance in a dispersed or dissolved form.

The phrase "interval therapy" refers to the administration of a fluid pharmaceutical agent at least once during a certain time period, for example, within minutes, hours, days, or weeks, in alternation with at least one other fluid pharmaceutical agent and/or physiological solvent.

The phrase "means for injection" refers to a device that can induce a flow or singular bolus of a solvent, and includes, for example, a pump, a syringe, a balloon, a piston, etc.

The phrase "needle screen" refers to a device for preventing an access port needle with a certain form or diameter from penetration from another access port needle with a similar or different form or diameter. The needle screen can be of any appropriate material known in the art, such as, for example, a netting material of appropriate diameter, or a foil with perforation of a certain diameter or form, etc.

The phrase "one way valve" refers to a device, such as a valve, for example, that allows fluid flow in substantially in only one direction.

The phrase "physiological solvent" refers to a fluid that is administered into the subject and is used in conjunction with or without a fluid pharmaceutical agent. A physiological solvent typically is of a composition that is physiologically compatible with the subject, and typically has a substantially similar pH and salt concentration as the target tissue or tumor. Illustratively, a physiological solvent is an aqueous solution of 0.9% sodium chloride at about a pH of about 6 to about 7.

The phrase "portable pump" refers to a pump having a weight and configuration that allows easy transport by the subject while maintaining the fluid flow rate characteristics that can be used with an apparatus described herein. For an adult human, for example, the maximum weight of a portable pump ranges, for example, from about less than about 1 kg to about less than 0.05 kg, or is less than about 0.75 kg, or less than about 0.5 kg, or less than about 0.25 kg, or less than about 0.1 kg, in an unfilled condition. Such portable pumps can be carried close to the body keeping the hands of the subject free, and can be secured to the body, for example, by a leather pouch fixed at the belt. Illustratively, a device such as a rolling stand, for example, is not needed when the patient is moving, thus providing full mobility while treatment is ongoing. Furthermore, in one embodiment of the present invention, the pump is easily maintainable, but robust enough to provide constant flows while the subject is moving in a manner appropriate during treatment (for example, walking, sitting, and/or laying). Additionally, in another embodiment, the portable pump is configured (for example, secured buttons and programs) such that there is substantially little or no danger of unintentional changes of the pump functions during daily-life activity. For ease of treatment and patient use, refilling of the solvent reservoir and reprogramming the pump should be simple and easy to understand without the need for any additional sophisticated devices, which is typical for an outpatient setting.

The term "proximal" refers to that part of the device that is downstream in the flow direction when viewed from the tumor or tissue into which the infusion catheter is implanted.

The term "septum" refers to a material covering the distal part of an access port enabling a needle to be inserted through it without loosing its seal around the needle or loosing its seal after the needle has been withdrawn. In one embodiment, the septum is pliable and capable of maintaining a seal after a needle has been inserted and withdrawn on one or more occasions.

The term "solvent" refers to a solvent such as a physiological fluid or a fluid pharmaceutical agent that can be infused with the device of the present invention.

The term "ventricular shunt" refers to fluid communication between intraspinal liquid and a body cavity, such as, for example, a vein or an intraperitoneal space, or a second access port system in fluid communication with, for example, an external solvent reservoir.

The present invention is further illustrated by the following examples, which should not be construed as limiting in any way.

EXAMPLES

Example 1

In this example, an isotropic 0.4% agarose gel model was used. (Chen Z-J, 2002). This gel was put into a transparent acrylic cube of 7 cm in length for a total volume of approximately 340 mL. Evans blue dye with a molecular weight of 960.8 was infused under carefully controlled conditions on the bench for a period of 24 hours and photographs were taken of the resultant infusion pattern. Images were taken at 0, 1, 3, 6, 12 and 24 hours of infusion time. The syringe pump used for in-subject treatment, Graseby 3200, (Sims Graseby Ltd, Watford, Herts, UK) was compared with the radial piston pump Pegasus Vario (Pegasus GmbH, Germany) using two different catheters. First a polyimide tube with 0.02 mm inner diameter and 0.85 mm outer diameter was used for the infiltration of the solvent. Secondly a ventricular catheter with multiple side holes (4 rows of 8 holes, for a total of 32 holes, from Promedics GmbH, Düsseldorf, Germany) was used for the infiltration.

Different flows were used. FIG. 4b depicts the distribution at a flow rate of 0.48 µL/h with the radial piston pump under test "Pegasus Vario." FIG. 4b depicts the corresponding distribution of the "Graseby 3200" syringe pump at the same flow rate of 0.48 mL/h.

Figure 4A:
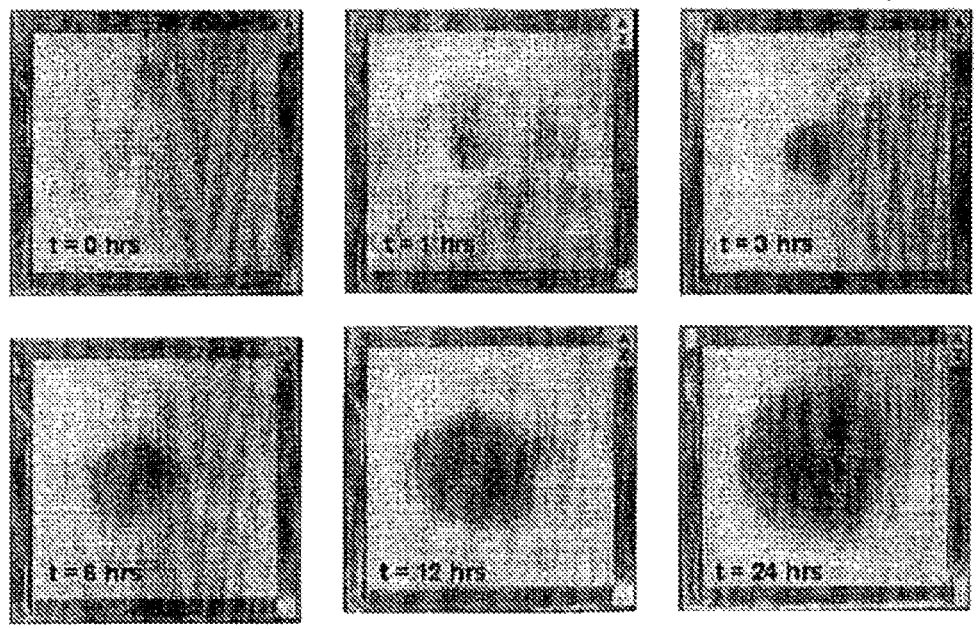

Surprisingly the "Pegasus Vario" radial piston pump, which has not been accepted for convection enhanced delivery purpose so far, showed distribution patterns over the time (FIG. 4b) as good as the convection enhanced delivery-approved syringe pump "Graseby 3200" did (FIG. 4a).

The experiment was also done with an average flow rate of 240 µL/h in which the results were comparable.

Example 2

For an application system for the treatment of glioma, a portable radial piston pump was used and included an infusing tube and the reservoir bag from LogoMed GmbH, Windhagen, Germany. The type of the portable pump was "Pegasus Vario" having a reservoir of polyurethane with a capacity of 50 mL. The infusing tube had a length of 100 cm in which a flat sterile filter (0.22 µm pore diameter) was integrated. An infusion needle, a Gripper®-needle (22G), with lengths of 16, 19, 25 and 32 mm was used from Smith Medical Deutschland GmbH, Kirchseeon, Germany). The access port PORT-A-CATH, low profile, made of titan, as well as the access port-catheter, were both purchased from Smiths Medical Deutschland, Kirchseeon, Germany. The access port catheter was made of silicon and impregnated with material to absorb x-rays and was connected with one infusion catheter (tumor catheter) by a CSF-catheter connector made of nylon from Promedics GmbH Düsseldorf, Germany.

As depicted in FIG. 1, the infusion catheter was surgically implanted with its perfusion holes ending in the brain in the center of the tumor (glioma), and was affixed on the scull. The access port chamber was connected with the access port catheter and was implanted on the subject's rib and the access port catheter was laid towards the open end of the infusion catheter, which was positioned in a manner cervically. The overlapping end of the access port catheter was shortened so that it was loose enough to follow movements of the body without influencing the exact position of the infusion catheter when connected and was then combined with the connector to the infusion catheter. All implanted devices were filled with a physiological solution prior to implantation.

The reservoir, pump head, infusion tubing and access port needle were filled with the solution that was infused, and the pump with the reservoir was positioned at an appropriate region of the body with, for example, a belt around the waist. The access port needle was then pricked through the skin the fatty tissue and the septum into the subcutaneously placed access port and then infusion was started.

The flow during the time the pharmaceutical active substance AP 12009 was administered varied between 200 µL/h and 500 µL/h for 4-7 days.

During the 7 days when no fluid pharmaceutical agent was administered the system was rinsed with 0.06 mL/h of isotonic sodium chloride solution. These cycles were repeated 6-13 times leading to a total time of the treatment of about half a year.

Example 3

This experiment was done to compare the flow characteristic of the convection enhanced delivery approved syringe Pump "Graseby® 3200" with the Portable Pump "Pegasus Vario." The measurement was performed at "Institut für Mikro- and Informationstechnik der Hahn-Schickard-Gesellschaft e. V.", Wilhelm-Schickard-Strasse 10, 78052 Villingen-Schwenningen, Germany.

The measurements were carried out at the "Liquid Flow" measuring site of this Institute.

To exclude external influences all measurements were carried out on a vibration damped desk.

In a first step the calibration curve of the sensor used for this experiment was calibrated applying the hydrostatic principle by which a flow is induced by connecting two tanks of different levels with tubes. The sensor used was SP45, type 300×600 tp 45, channel 0.8 mm×0.4 mm, heating power 20 mW (20V).

The pumps were measured in combination with the devices that were used in Example 1. Briefly, the pump with the reservoir was connected with the infusing tube with a filter and an access port needle, access port, access port catheter, connector and infusion catheter. To be appropriately connectable with the test device, the infusion catheter was shortened in length just behind the perfusion holes viewed from the tip. The fluid used for the test system was water.

The results of the flows measured in this experiment are depicted in FIGS. 2a and 2b for the syringe pump "Graseby® 3200" and in FIGS. 3a and 3b for the "Pegasus Vario."

For all formulations herein, doses may be compounded as is known in the art.

The invention has been described in an illustrative manner, and it is to be understood the terminology used is intended to be in the nature of description rather than of limitation. All patents and other references cited herein are incorporated herein by reference in their entirety. Many modifications, equivalents, and variations of the present invention are possible in light of the above teachings, therefore, it is to be understood that within the scope of the appended claims, the invention may be practiced other than as specifically described.

What is claimed is:

1. An apparatus comprising:
   a. an extracorporeal solvent reservoir comprising a distal portion, a proximal port and a lumen extending therethrough;
   b. an extracorporeal portable pump comprising a proximal port and a distal port and a lumen therethrough wherein the extracorporeal portable pump is in fluid communication with the extracorporeal solvent reservoir;
   c. an infusion catheter configured for insertion into the tumor of the subject, the infusion catheter comprising a length extending from a proximal end for introduction into the tumor to a distal end with a lumen extending between the proximal end and the distal end wherein the infusion catheter is in fluid communication with the solvent reservoir and portable pump;
   d. an intracorporeal access port comprising an access port casing, two or more access port chambers defined within the casing, each access port chamber having a proximal port, a distal port and a lumen extending therebetween, a pliable septum covering the distal port of each chamber, wherein the intracorporeal access port is located proximal from the extracorporeal portable pump and facilitates fluid communication between
      (i) the extracorporeal solvent reservoir and extracorporeal portable pump, and
      (ii) the infusion catheter; and
   e. means for convection enhanced delivery of a solvent to a target tumor, wherein the solvent delivered by convection enhanced delivery has (i) a flow rate at the target tumor of more than 0.001 ml/h and less than 1 ml/h; (ii) a total flow volume within one period of any oscillation of less than about 0.5 µl; and (iii) an amplitude of oscillation between about 0.05 ml/h and about 1 ml/h.

2. The apparatus of claim 1, further comprising:
   a. at least one access port catheter comprising a proximal port, a distal port, and a lumen extending therethrough, wherein the proximal port of the access port catheter is in fluid communication with (i) the infusion catheter lumen and (ii) one of the distal ports of the access port chambers;
   b. at least one infusion tube configured for connection to one of the distal ports of the access port chambers, the infusion tube comprising a length extending from a proximal end for introduction into the distal end of the access port chamber, to a distal port opposite the proximal end, and a lumen extending therethrough.

3. The apparatus of claim 2, further comprising a filter system.

4. The apparatus of claim 3, wherein the filter system comprises one or more separate filters.

5. The apparatus of claim 4, wherein the filter system comprises a sequence of two or more filters.

6. The apparatus of claim 5, wherein the filter system comprises filters placed in a sequence, from upstream to downstream, of an air filter, a particle filter, and a sterile filter.

7. The apparatus of claim 4, wherein each separate filter comprises a distal port, a proximal port, a lumen therethrough, and a membrane disposed within the lumen.

8. The apparatus of claim 4, wherein the one or more filters are a sterile filter for removing pathogens, a biological filter for removing biological material, a particle filter for removing particulates, a chemical filter for removing chemicals, or a filter for removing gasses from the solvent.

9. The apparatus of claim 4, wherein the filter system comprises a filter having a pore size of about 0.45 µm or less.

10. The apparatus of claim 4, wherein the filter system comprises a filter having a pore size of about 0.22 µm or greater.

11. The apparatus of claim 4, wherein the filter system comprises a filter having a pore size of about 0.45 µm or greater.

12. The apparatus of claim 2, further comprising two or more infusion catheters, and a distributor disposed between the proximal port of the access port catheter and the distal ends of the two or more infusion catheters.

13. The apparatus of claim 12, wherein the distributor comprises a plurality of proximal ports, equivalent to the number of infusion catheters, a distal port, and an interconnected lumen disposed there between,
   wherein the distal port of the distributor is connected to, and in fluid communication with, a proximal port of the access port catheter, and
   wherein the proximal ports of the distributor are connected to, and in fluid communication with, the distal ends of the two or more infusion catheters.

14. The apparatus of claim 13, wherein the equivalent internal diameters of the distributor's proximal ports are less than the internal diameter of the distributor's distal port.

15. The apparatus of claim 13, wherein the internal diameters of the each of the proximal ports of the distributor are different from each other.

16. The apparatus of claim 2, wherein the two or more access port chambers are configured to be penetrated by a needle one or more times without loosing fluid containment integrity.

17. The apparatus of claim 16, wherein the infusion tube further comprises an access port-needle at the proximal port of the infusion tube adopted for insertion into one of the distal ports of the access port chambers.

18. The apparatus of claim 2, wherein the access port further comprises a distal access port chamber disposed above a proximal access port chamber, wherein the septum for the proximal access port chamber is integrated into the bottom of the distal access port chamber and separates the proximal and distal access port chambers.

19. The apparatus of claim 18, wherein the access port further comprises a needle screen located on the bottom of the distal access port chamber, adjacent to, and covering, the septum of the proximal access port chamber.

20. The apparatus of claim 2, further comprising a ventricular shunt in fluid communication with the access port system.

21. The apparatus of claim 2, further comprising an expanding volume having a lumen in fluid communication with a lumen downstream of the portable pump.

22. The apparatus of claim 2, wherein at least one of the infusion catheter, the infusion tube, and the access port catheter are made from polyvinylchloride material.

23. The apparatus of claim 2, wherein the lumen of the infusion catheter, infusion tube, and access port tube has an inner diameter of between about 0.1 mm to about 5 mm.

24. The apparatus of claim 1, wherein the infusion catheter further comprises a plurality of perfusion holes.

25. The apparatus of claim 24, wherein the infusion catheter further comprises a marker wire to allow for monitoring the position of the infusion catheter.

26. The apparatus of claim 24, wherein the lumen of the infusion catheter comprises a plurality of separate lumens.

27. The apparatus of claim 24, wherein the infusion catheter further comprises a fixation device attached thereto, for affixing the infusion catheter to a solid tissue or bone.

* * * * *